(12) United States Patent
Nilsson et al.

(10) Patent No.: US 12,216,114 B2
(45) Date of Patent: Feb. 4, 2025

(54) ISOLATED ORGAN EVALUATION AND TREATMENT

(71) Applicant: XVIVO Perfusion AB, Gothenburg (SE)

(72) Inventors: Magnus Nilsson, Gothenburg (SE); Anne-Li Sigvardsson, Gothenburg (SE)

(73) Assignee: XVIVO PERFUSION AB, Gothenburg (SE)

( * ) Notice: Subject to any disclaimer, the term of this patent is extended or adjusted under 35 U.S.C. 154(b) by 675 days.

(21) Appl. No.: 17/150,202

(22) Filed: Jan. 15, 2021

(65) Prior Publication Data

US 2021/0132044 A1    May 6, 2021

Related U.S. Application Data

(63) Continuation of application No. 15/580,901, filed as application No. PCT/EP2016/064645 on Jun. 24, 2016, now abandoned.

(30) Foreign Application Priority Data

Jun. 25, 2015 (GB) ..................... 1511207

(51) Int. Cl.
  *A01N 1/02* (2006.01)
  *G01N 33/50* (2006.01)
  *G01N 33/68* (2006.01)

(52) U.S. Cl.
  CPC ......... *G01N 33/5082* (2013.01); *A01N 1/021* (2013.01); *A01N 1/0226* (2013.01); *G01N 33/6893* (2013.01)

(58) Field of Classification Search
  CPC ... G01N 33/5082; A01N 1/021; A01N 1/0226
  See application file for complete search history.

(56) References Cited

U.S. PATENT DOCUMENTS

| | | |
|---|---|---|
| 9,835,630 B2 | 12/2017 | Keshavjee et al. |
| 2011/0076666 A1 | 3/2011 | Brassil |
| 2012/0315618 A1 | 12/2012 | Kravitz et al. |

FOREIGN PATENT DOCUMENTS

| | | |
|---|---|---|
| CN | 101199273 B | 4/2011 |
| WO | 87/06836 A1 | 11/1987 |
| WO | 0124793 A1 | 4/2001 |
| WO | 02/17714 A2 | 3/2002 |
| WO | 02/35929 A1 | 5/2002 |
| WO | 2008001096 A2 | 1/2008 |
| WO | 2011/097541 A2 | 8/2011 |
| WO | 2012027787 A1 | 3/2012 |
| WO | 2015/042602 A1 | 3/2015 |

OTHER PUBLICATIONS

Feng, S. American Journal of Transplantation 10:1155-1162. (Year: 2010).*
Wahn et al., "Inhibition of PMN-and HOC1-indeed vascular injury in isolated rabbit lungs by acetylsalicylic acid: a possible link between neutrophil-derived oxidative stress and eicosanoid metabolism?", Biochimica et Biophysica Acta. Molecular Basis of Disease, Amsterdam, vol. 1408, No. 1, pp. 55-66, Oct. 22, 1998.
Werrmann et al., "Comparison of Effects of Angiotensin-Converting Enzyme Inhibition with Those of Angiotensin II Receptor Antagagonism on Functional and Metabolic Recovery in Postischemic Working Rate Heart as Studies by [31P] Nuclear Magnetic Resonance", Journal of Cardiovascular Pharmacology, Raven Press, New York, NY, US, vol. 24, No. 4, pp. 573-586, Jan. 1, 1994.
Seymour et al.,. "In Vitro Hepatic Insulin Resistance in Chronic Pancreatitis in the Rat", Journal of Surgical Research, Academic Press Inc., San Diego, CA, US, vol. 46, No. 5, pp. 450-456, May 1, 1989.
European Medicines Agency: "Consultation procedure Public Assessment Report (CPAR): Steen solution", European Union, pp. 1-20, Aug. 8, 2012.
Extended European Search Report for European Application No. 20 21 2381 dated Mar. 30, 2021.
Gnadt, et al., "Surfactant Protein A (SP-A) and Angiotensin Converting Enzyme (ACE) as Early Biomarkers for Pulmonary Edema Formation in Ventilated Human Lung Lobes," Lung, 2012, vol. 190, Issue 4, pp. 431-440.
Klocking, et al., "Studies on the Release of Plasminogen Activator From the Isolated Rat Lung by Serine Proteinases," Thrombosis Research, 1981, vol. 23, pp. 375-379.
Kuck, et al., "Mitochondrial DNA damage-associated molecular patterns mediate a feed-forward cycle of bacteria-induced vascular injury in perfused rat lungs," Am J Physiol Lung Cell Mol Physiol, 2015, vol. 308, pp. L1078-L1085.
Muellbacher, et al., "Regulation of plasminogen activation in isolated perfused rat kidney," American Journal of Physiology Renal Physiology, 1989, vol. 256, Issue 5, pp. F787-F793.
Tanswell, et al., "Nonlinear Pharmacokinetics of Tissue-Type Plasminogen Activator in Three Animal Species and Isolated Perfused Rat Liver," The Journal of Pharmacology and Experimental Therapeutics, 1990, vol. 255, Issue 1, pp. 318-324.
International Search Report and Written Opinion issued in international application No. PCT/EP2016/064645 dated Sep. 29, 2016, 16 pages.
Taylor et al., "Current State of Hypothermic Machine Perusion Preservation of Organs: The Clinical Perspective," Cryobiology, available in PMC Jul. 1, 2011, pp. 1-38 (published in final edited from as Cryobilogy (Jul. 2010), vol. 60 (3S); S20-S35 (doi:10.1016/j.cryobiol.2009.10.006).
Russo, et al., "Addition of Simvasatatin to Cold Storage Solution Prevents Endothelial Dysfunction in Explanted Rat Livers", Hepatology, 2012, vol. 55, No. 3, pp. 921-930.

(Continued)

*Primary Examiner* — Diana B Johannsen
(74) *Attorney, Agent, or Firm* — Pearne & Gordon LLP

(57) ABSTRACT

The present invention relates to methods of evaluating and/or treating organs during isolated organ perfusion, and kits for carrying out this evaluation.

17 Claims, No Drawings

(56) References Cited

OTHER PUBLICATIONS

Song, et al., "Pretreatment With Calcitonin Gene-Related Peptide Attenuates Hepatic Ischemia/Reperfusion Injury in Rats", Transplanstation Proceedings, 2009, vol. 41, pp. 1493-1498.

Bejaoui, et al., "Emerging concepts in liver graft preservation", World Journal of Gastroenterology, Jan. 14, 2015, vol. 21, No. 2, pp. 396-407.

Hosgood, et al., "Normothermic machine perfusion of the kidney: better conditioning and repair?," Transplant International, 2014, vol. 28, pp. 657-664.

Holland, et al., "Calcitonin Gene-Related Peptide Reduces Brain Injury in a Rat Model of Focal Cerebral Ischemia," Stroke, 1994, vol. 25, pp. 2055-2058.

* cited by examiner

ISOLATED ORGAN EVALUATION AND TREATMENT

CROSS-REFERENCE TO RELATED APPLICATIONS

This application is a continuation of U.S. application Ser. No. 15/580,901, filed Dec. 8, 2017, which is a national stage application of International Application PCT/EP2016/064645, filed Jun. 24, 2016, and which claims priority of United Kingdom Patent Application No. 1511207.1, filed Jun. 25, 2015, all of which are incorporated herein by reference.

FIELD OF INVENTION

The present invention relates to methods of evaluating and treating organs during isolated organ perfusion, and kits for carrying out this analysis.

BACKGROUND TO THE INVENTION

Organs that can be transplanted from one person or animal to another include the heart, kidneys, liver, lungs, pancreas and bowels. Kidney transplants are most commonly performed. Transplants of the heart, liver and lungs are also regularly carried out. However, there are many more people in need of organ transplants than organs available and, tragically, many people die while waiting for a suitable organ.

It is very important that organs are kept in the best possible condition between harvesting and transplantation. In order to maintain the organ in the best possible condition, the organ can be isolated from the blood circulation of the donor, and perfused with a Perfusate. For example, ex vivo lung perfusion (EVLP) is today considered a safe procedure with the capacity to increase the number of lungs available for transplantation. More than 350 transplantations have been performed after EVLP. However, the procedure is only carried out at a few lung transplantation centers around the world.

In order to have more available lungs to save more patients with terminal lung diseases, the technique needs to be adopted by more centers. However, one of the current difficulties is that methods for evaluating an organ to determine whether or not it is suitable for transplantation are not very advanced. Wider adoption of this technique would be more likely if objective data was available to determine whether or not to use the organ for transplantation.

An isolated organ perfusion procedure today involves removing an organ such as a lung or lungs from a donor and connecting it to a perfusion circuit, comprising a pump(s), a reservoir, a heater cooler, an oxygenator and a ventilator. If the organ is another organ than a lung, a ventilator is not used. The vasculature of the organ is pumped with a Perfusate. The Perfusate might be, for example, STEEN Solution (see WO2002/035929) or another solution appropriate for organ perfusion. The solution might contain erythrocytes and it might be oxygenated. EVLP is only one form of isolated organ perfusion. Other solid organs like heart, kidney, liver, pancreas, and small bowels can also be perfused in an ex vivo organ perfusion model (EVOP). Furthermore, an organ can be circulatorily isolated while remaining within the body in an in vivo isolated perfusion (IVIP). The isolated perfusion can also be extended to comprise a hand, arm, leg or any other body part that can be temporarily circulatorily isolated.

Different organ specific parameters can be evaluated during the perfusion but to date these have mainly been physical parameters. For example, if the organ is a lung, parameters such as pulmonary vascular resistance (PVR), compliance and oxygenation capacity have been monitored. While these parameters provide some information to the user, they do not give definitive information about whether or not an organ should be selected for transplant and so the decision to transplant or not is still largely based on subjective evaluation. Therefore, there is an urgent need for additional objective parameters that could be used to determine the quality of an organ during an organ perfusion evaluation.

The focus on molecular biomarkers in the literature has been related to interleukin signalling, especially IL-1β, IL.6, IL-8, IL-10 and TNFα. However, despite several publications these markers have not been shown to be useful in a clinical setting. One reason being that they are generally not analyzed with point-of-care (PoC) methods and therefore the information, even if clinically valuable, is not available to the Clinicians when the decision to transplant or not has to be made. An EVLP procedure normally lasts between 2 and 6 hours, and information not available in this time frame is of no use in informing the decision as to whether or not to transplant that organ.

Furthermore, Ischemia Reperfusion Injury (IRI) is a well-known complication to organ transplantation. It occurs at the time of recirculation of the organ with oxygenated blood. Although an acute phase reaction, the effects of this early injury are believed to be a significant contributor to later morbidity and mortality in the organ recipients. A better ability to select and de-select organs for transplantation could alleviate IRI and improve survival and health in the recipients both in short and long term.

SUMMARY OF THE INVENTION

According to a first aspect, the present invention relates to a method of evaluating an organ during isolated organ perfusion, the method comprising the steps of: perfusing the isolated organ with a Perfusate; and measuring the concentration in the Perfusate of one of more biomarkers including at least one biomarker selected from the group consisting of TF, tPA, SpA, SpD, or a cell rupture marker.

According to a second aspect, the present invention relates to a method of treating an organ during isolated organ perfusion, the method comprising the step of perfusing the isolated organ with a Perfusate, wherein the Perfusate comprises a TF suppressor molecule.

According to a third aspect, the present invention relates to the use of a TF suppressor molecule to down regulate TF expression during an isolated organ perfusion.

According to a fourth aspect the present invention relates to a kit for analysis of a Perfusate during isolated organ perfusion, the kit comprising an immunologic analysis for TF, tPA, dsDNA, SpA or SpD or a chromogenic analysis for TF or tPA or a Picogreen analysis for dsDNA.

Accordingly, the present invention provides a much-needed method of evaluating an organ in an objective way by measuring the concentration in the Perfusate of one or more key biomarkers that can indicate the health of the organ. Further information about each of the biomarkers is given below.

The isolated organ can be from an animal or a human being, and is usually a lung or lungs, a kidney, a liver, a heart, a pancreas or a bowel. By isolated, we mean that the organ is isolated from the circulatory system. It can be isolated in vivo or isolated ex vivo as is already known in organ perfusion. It is then perfused with a Perfusate and the Perfusate can be analysed. Specifically, the concentration in the Perfusate of one or more biomarkers is measured. The present invention relates specifically to measuring at least one of the following biomarkers, TF, tPA, SpA, SpD, or a cell rupture marker such as double stranded DNA (dsDNA), mitochondrial DNA, or ribosomes.

A single measurement of the concentration of the biomarker can be taken, but it is preferable that the concentration of the one or more biomarkers is measured continuously over a predetermined time period or repeatedly at predetermined intervals, this is preferably throughout the perfusion period which is usually between 1 and 6 hours.

In order to use the method for evaluating the organ in practice, the measured concentrations in the Perfusate of the one or more biomarkers are compared against reference values, and the organ is then selected or deselected on the basis of how the measured concentrations compare with the reference values. This gives the clinician an objective parameter to use to determine whether or not the organ is suitable for transplantation. While the concentration of just one of the selected biomarkers can give valuable information in evaluating an organ, this method is particularly valuable where the concentration of at least two of the biomarkers is measured. The combinatorial analysis can lead to particularly good predications of which organs will and will not be successful for transplantation, and can be used to thus improve patient outcomes.

Additionally, the isolated organ can actually be treated according to how the measured concentrations of biomarker compare to reference values. If certain conditions are met, the isolated organ can be treated by adding a component to the Perfusate. Advantageously, the treatment effect of the component on the isolated organ can be monitored by further evaluation. An example of this is that a TF suppressor molecule can be added to the Perfusate to down regulate TF expression when the measured concentration of TF exceeds reference value. Further examples for the different specific biomarkers are discussed below.

The present invention also relates to methods of treating an organ during isolated organ perfusion. As discussed below, it is highly probable that the organ has been subjected to stress, simply from the negative effects of brain death or from ceased circulation in a non-heart beating donor. Accordingly, the organ can be treated independently from evaluation, for example by adding a TF suppressor molecule to the Perfusate to down regulate TF expression. This has the advantage that treatment can commence immediately, and is usually used in conjunction with evaluation, i.e. treatment is prior to or during evaluation.

The overarching aim of the present invention is to improve the success rate of transplants, in order to improve quality of life for patients. Another overarching aim is to treat organs so that more organs can be successfully transplanted and more people can benefit from organ transplants. The organs are generally transplanted into another person, and are not transplanted back into the donor.

Description

A peculiarity with isolated organ perfusion and even more so with isolated organ perfusion using a defined solution such as STEEN Solution as the Perfusate, is that no other organ systems are present. This provides a unique opportunity to investigate an organ system, but at the same time, the physiology is abrupt. Very little is actually known about how an isolated organ responds to its un-physiological environment. It could be anticipated that the organ initiates its normal physiological reactions to for example inflammation and coagulation, but what happens when the organ is not receiving the external responses anticipated in an in vivo situation. This is a field of research that is largely unexplored.

Perfusates are known to the skilled person such as STEEN solution. Any suitable Perfusate can be used in the present invention. Isolated organ perfusion is generally not done with a full blood Perfusate. One main reason for this is that blood contains several enzymatic systems that when activated could harm the organ. Examples of these systems are coagulation and complement activation. The organ has already been under stress in the donor and is more or less damaged from systemic effects of brain death or circulatory arrest. This existing damage could activate these enzymatic systems and further harm the organ. Immune cells present in whole blood are also particularly harmful during these circumstances. Therefore, a solution like STEEN Solution, comprising physiological salts, dextran and albumin is considered safer for the organ. As none of the enzymatic systems nor any blood derived immune cells other than those resident within the organ are present, the organ is given a chance to heal and regain function during optimal conditions.

This relatively pure system allows investigation of the molecular signalling done by the organ itself and immune cells that the organ is hosting, without disturbances from signalling from other sites.

Not only does this system provide an opportunity to evaluate the function of the organ, it also offers an opportunity to treat the organ. During isolated perfusion the organ can be treated with normal or elevated doses of pharmaceuticals or biologicals as no systemic side effects will occur.

Tissue Factor-Background

Tissue Factor (TF) is a transmembrane protein, of 46 KDa when in full length. During normal circumstances TF is not exposed to blood. It is expressed and or exposed to blood when an injury to the vascular endothelium has occurred. The expression of TF is higher in organs with a high vascular content as brain and lung tissue. TF exposed to blood binds and activates Factor VII (FVII) to FVIIa. FVIIa remains bound to TF and this interaction enhances the activity of FVIIa $2 \times 10^7$ fold. TF and FVIIa then activate the zymogens Factor IX (FIX) and Factor X (FX) to FIXa and FXa. FXa and FIXa bind to their respective cofactors Factor Va and Factor FVIIIa. FXa activates prothrombin (FII) to thrombin and thrombin cleaves fibrinogen to fibrin monomers which polymerizes to form blood clots. TF is therefore a powerful initiator of blood coagulation.

Endothelial cells are activated to produce TF upon stimulation with pro-inflammatory cytokines such as Tumor necrosis factor alpha (TNFα), Interleukin 1 β (IL-1β) and CD40 ligand and also with activation from biogenic amines such as histamine or serotonin and by oxidized LDL and VEGF (see Steffel et al 2006). Monocytes and macrophages are also activated to produce TF by pro-inflammatory cytokines and endotoxins. Circulated TF is found in microparticles which are released from endothelial cells, vascular smooth muscle cells and monocytes. This provides a source of TF factor that is absorbed by platelets, which has no own production of TF. A differently spliced form of TF produces a pro-coagulant TF that is released in a free form to the circulation. This form of TF is stimulated by cytokines.

TF is also pro-inflammatory and plays a crucial role in the coagulation-inflammation-thrombosis circuit. This circuit has been implied in many conditions such as cancers, diabetes, obesity, sepsis, DIC, cardiovascular dysfunction or atherosclerosis etc.

TF is believed to be expressed by monocytes, macrophages and granulocytes upon stimulation and soluble Tissue Factor (sTF) is released from endothelial cells upon stimulation of pro-inflammatory cytokines. Upregulation or exposure of TF is known to be stimulated by LPS, ILs, TNFα, IFN etc. It is also known to be upregulated during hypoxia.

Membrane fragments from damaged tissue comprising TF is another source of circulating TF.

Down regulation of TF is known to occur upon exposure to HMG-CoA reductase inhibitors, cyclooxygenase (COX) inhibitors, paclitaxel, lysophosphatidylcholine, insulin, nicotinamide, nitric oxide (NO)/or soluble guanylate cyclase activator, hydroxyurea, ethyl pyruvate, dimethyl sulfoxide (DMSO), angiotensin converting enzyme (ACE) inhibitors, adiponectin, retinoic acid, all-trans retinoic acid, vitamin D3, PGJ2, PPARα agonists activators (WY14643 and eicosatetraenoic acid), liver X receptor agonists, pentoxifylline, phenolics/resveratrol derivatives, indobufen, amiodarone, metformin, elevated intracellular cAMP, and PI3K/Akt/PKB signalling etc. Other known ways to down regulate TF are to use miR-19, short hairpin RNA, hairpin ribozyme, or anti sense ODN.

TF has been suggested to be involved in lung injury in Acute Respiratory Distress Syndrome (ARDS). Humanized anti TF antibodies have been shown to ameliorate lung injury in a human TF knock-in mouse ARDS model (see He et al 2008). It has also been mentioned that TF is upregulated after IRI (see Yamane et al 2005) although data was not shown. TF has been shown to be upregulated in heart transplant recipients developing Cardiac Allograft Vasculopathy (see Yes et al 2002). Pentoxifylin was shown to prevent upregulation of monocyte TF in renal transplant recipients and improved graft function (see Susen et al 2000). However, none of the mentioned references were related to isolated organ perfusion. The evaluation or treatment of an organ during isolated perfusion has not before been associated with TF.

Tissue Factor—In the Invention

TF was shown by the inventors to be present in the Perfusate during EVLP. It increased with time and more so in lungs that were not considered transplantable. This shows that TF is an important biomarker of lung function during EVLP. As TF is released by vasculature, tissue and immune cells it is anticipated that the same situation is relevant for other solid organs to be transplanted, such as hearts, livers, pancreas, bowels and kidneys. Hence analysis of TF in the Perfusate from an organ during isolated organ perfusion is a biomarker for organ function and well-being. Isolated organ perfusion can be an in vivo procedure, where the organ is still in the body, but the circulation has been isolated. Such a procedure could for example be used for cancer therapy, or for other therapies where adverse reactions in other organs or systemically should be avoided. Furthermore, TF analysis could be used as a parameter to decide how to treat the organ during the isolated perfusion whether in vivo or ex vivo.

TF could be analyzed through either immunological or activity assays. With the technology available today an activity assay would be preferred as the concentration of TF in the Perfusate is within the pico to nano gram scale. Such low concentration adopts well for activity-based assays. However, as the immune based assay technology is likely to evolve further, a PoC immune assay may be contemplated. In any case the assay used should deliver results within about an hour or more preferably within 30 minutes to be useful during the actual procedure.

An activity assay utilizes the enzymatic amplification systems that are driven by the factor analyzed for. In the case of TF, such an assay could be based on FVII, FIX, FX or FII activation and measurement of substrate cleavage. For example, TF activity could be measured through addition of FVII which is activated by TF to FVIIa and substrate to FVIIa. The enzymatic cleavage of the FVIIa substrate could be monitored either kinetically or after a stopped reaction. The substrate could be a chromogenic substrate. A more amplified assay would in addition to FVII comprise FX. In this case the TF/FVIIa complex activates FX to FXa and the FXa activity is monitored with FXa substrate. The enzymatic cleavage of the FXa substrate could be monitored either kinetically or after a stopped reaction. The substrate could be a chromogenic substrate. In an even further amplified, although more complex assay also FII activation could be used and monitoring would then be done with a FII substrate either in a kinetic or a stopped reaction.

TF could be measured once or repeatedly during isolated organ perfusion. The isolated organ perfusion could be an EVOP, an EVLP, an in vivo isolated organ perfusion (IVIOP) or in vivo isolated lung perfusion (IVILP). The measurements could for example be made every ½ hour or every hour or every second hour of the EVOP, IVIOP or more specifically EVLP or IVILP.

The TF measured in the Perfusate could be of any origin. For example, it could be present as membrane micelles released from dying cells or from cells under shear stress. It could be soluble TF (sTF) released from the membranes or directly produced through alternative splicing patterns or it could be bound to circulation immune cells within the Perfusate, such as monocytes or granulocytes or any other origin.

As TF is a marker for both a hyper-coaguable state and a pro-inflammatory state, an increase of TF is a marker of an adversely effected organ function post-transplant and the level can be used as an indicator of whether an organ should be transplanted or not. Furthermore, the information about elevated TF levels could be used to monitor status of an organ during IVIOP or specifically IVILP. TF can be used as a signal to induce therapies reducing TF activity and/or expression and thereby improve the organ. As TF is generally somewhat augmented during isolated perfusion, this therapy could be initiated independent of the analysis however the effects of the therapy could then be followed during the isolated organ perfusion as reduction in TF concentration in the Perfusate.

A TF therapy could include depletion with a TF antibody to remove the already formed TF. More preferably the therapy could include use of a substance that down regulates expression of TF. In this embodiment of the invention a TF suppressor molecule is added to the Perfusate when the measured concentration of TF exceeds a reference value. Such TF suppressor molecules are known in the prior art and could for example be selected among HMG-CoA reductase inhibitors, cyclooxygenase (COX) inhibitors, paclitaxel, lysophosphatidylcholine, insulin, nicotinamide, nitric oxide (NO)/or soluble guanylate cyclase activator, hydroxyurea, ethyl pyruvate, dimethyl sulfoxide (DMSO), angiotensin converting enzyme (ACE) inhibitors, adiponectin, retinoic acid, all-trans retinoic acid, vitamin D3, PGJ2, PPARα agonists activators (WY14643 and eicosatetraenoic acid), liver X receptor agonists, pentoxifylline, phenolics/resveratrol derivatives, indobufen, amiodarone, metformin, elevated intracellular cAMP, and PI3K/Akt/PKB signalling etc. or equivalents of any of those molecules. Other known ways to down regulate TF is to use, miR-19, short hairpin RNA, hairpin ribozyme, or antisense ODN.

The down regulation of TF could be done using physiological accepted doses of one or more of the above-mentioned molecules alone or in combination. As the organ is circulatorily isolated an elevated concentration of one or more of the above-mentioned molecules could be used without causing systemic adverse events.

Preferably the down regulating molecule of TF is selected among COX-inhibitors, Paclitaxel, retinoic acid, vitamin D3, resveratrol derivate, indobufen, amiodarone or metformin or a combination thereof or equivalents of any of these substances.

The concentration of COX-inhibitors could for non-selective COX inhibitors such as aspirin, naproxen and ibuprofen or their equivalents be used in concentrations between 1 mg/l Perfusate and 10 g/l Perfusate, more preferably between 10 mg/l Perfusate and 2 g/l Perfusate, furthermore preferably between 150 mg/l Perfusate and 1000 mg/l Perfusate.

Selective COX-2 inhibitors such as Celecoxib, Rofecoxib and other COX-2 selective NSAIDs could be used in concentrations between 1 mg/l Perfusate and 10 g/l Perfusate, more preferably between 10 mg/l Perfusate and 2 g/l Perfusate, furthermore preferably between 50 mg/l Perfusate and 500 mg/l Perfusate.

The concentration of Paclitaxel or its equivalents could be between 1 mg/l Perfusate and 10 g/l Perfusate, more preferably between 10 mg/l Perfusate and 2 g/l Perfusate, furthermore preferably between 15 mg/l Perfusate and 500 mg/l Perfusate.

The concentration of Retinoic acid could be between 0.1 mg/l Perfusate and 1 g/l Perfusate, more preferably between 0.5 mg/l Perfusate and 500 mg/l Perfusate, furthermore preferably between 1 mg/l Perfusate and 100 mg/l Perfusate.

The concentration of Vitamin D3 could be between 0.1 µg/l Perfusate and 100 mg/l Perfusate, more preferably between 1 µg/l Perfusate and 100 mg/l Perfusate, furthermore preferably between 1 µg/l Perfusate and 1 mg/l Perfusate.

The concentration of Indobufen or its equivalents could be between 1 mg/l Perfusate and 10 g/l Perfusate, more preferably between 10 mg/l Perfusate and 2 g/l Perfusate, furthermore preferably between 15 mg/l Perfusate and 1000 mg/l Perfusate.

The concentration of Amiodarone or its equivalents could be between 1 mg/l Perfusate and 10 g/l Perfusate, more preferably between 10 mg/l Perfusate and 2 g/l Perfusate, furthermore preferably between 15 mg/l Perfusate and 1.2 g/l Perfusate.

The concentration of Metformin or its equivalents could be between 1 mg/l Perfusate and 50 g/l Perfusate, more preferably between 10 mg/l Perfusate and 10 g/l Perfusate, furthermore preferably between 100 mg/l Perfusate and 5 g/l Perfusate.

Abbreviation of the vicious coagulation-inflammation cycle dependent on TF, with TF suppression therapy during isolated organ perfusion, would not only improve the immediate organ function, but also the function at a later stage. In organ transplantation the initial damage after reperfusion IRI, is a determinant of the future survival and health of the recipient. For lung transplantation, IRI is considered to be a determinant of development of Broncho Obliterans Syndrome (BOS), rejection and other form of organ dysfunction several years from transplantation. Less IRI achieved through TF therapy would therefore be of long lasting effect in the recipient.

Either a specific cut-off reference value for acceptable concentration of TF could be used or the concentration could be followed over time during the isolated organ perfusion and the changes could be used to decide if the organ is well functioning or not or if it is responding to treatment. The analysis could be used on its own or in combination with other analysis. A combinatorial approach could improve sensitivity and/or specificity of the analysis as more organ functions are being tested.

For example, a cut off reference value for the concentration of TF in the Perfusate could be above 50 pg/ml, or above 75 pg/ml or above 100 pg/ml or above 130 pg/ml or above 150 pg/ml or above 175 pg/ml or above 200 pg/ml. Above these values the organ could be deselected for transplantation or a decision could be made to treat the organ by adding a molecule such as a TF suppressor molecule to the Perfusate.

Tissue Plasminogen Activator—Background

Tissue Plasminogen activator (tPA) is an activator of the serine protease Plasminogen. Activated plasminogen, plasmin, lyses blood clots, through fibrin degradation. TPA is thus part of the fibrinolytic system. Blood clots and microthrombi are often collected in the lungs as the lungs function as a filter for clots before the blood enters the systemic circulation. The lung is relatively resistant to this as it is oxygenated from both air and blood circulation. Nevertheless, the clots and microthrombi need to be cleared out continuously. This clearance involves tPA activation of Plasminogen. Therefore, tPA is released from the endothelium of the lung in response to clots or microthrombi. Endothelium elsewhere also releases tPA to activate Plasminogen and there is a need in all tissue and organs to clear blood clots and microthrombi.

Urokinase, an alternative plasminogen activator was used during EVLP in a study by Inci et al 2007. This was done without being related to the level of tPA in the Perfusate. This study showed that use of urokinase during EVLP improved the lung function in lungs from non-heart beating donors (NHBDs). Organs from NHBDs are known to contain more clots and microthrombi as circulation has ceased in the donor. On the other hand, Zhao et al 2010 showed that tPA depletion attenuates ischemic reperfusion injury in a mouse model. TPA has not before been measure in the Perfusate during isolated organ perfusion.

Tissue Plasminogen Activator—In the Invention

The present inventors understand that tPA in the Perfusate could be considered a marker of a fibrinolytic state in the perfused organ. All organs are likely to have some degree of clots or microthrombi and therefore an endothelial response with release of tPA could be considered as a normal functioning organ response. If the tPA response is not adequate it could mean that the endothelium is not healthy enough to respond. However, if the response is hyper-elevated it could suggest that the organ is heavily circulatorily restricted with blood clots. Therefore, it is suggested that a healthy organ should respond with a moderate elevation of tPA during isolated organ perfusion. As the lung functions as a filter for blood clots and microthrombi from the circulation, it generally contains more clots and microthrombi than other organs and is therefore especially dependent on fibrinolysis.

Although, the inventors have shown this effect in lungs, all organs contain vasculature and therefore releases tPA to the Perfusate and the same relations is anticipated.

The analysis of tPA could be done with immunological methods or as an activity assay. In any case the assay used should deliver results within about an hour or more preferably within 30 minutes to be useful during the actual procedure. If an activity assay is used, the activity could be measured using a tPA substrate directly or through addition of Plasminogen and measuring the resulting plasmin activity with a plasmin substrate. The tPA or plasmin substrate could be a chromogenic substrate.

If tPA activity in the organ is not considered sufficient after analysis a fibrinolytic agent could be included in the Perfusate. This fibrinolytic agent could for example be tPA, streptokinase or urokinase. The concentration of the fibrinolytic agent could be between 0.1 µg/l Perfusate and 100 mg/l Perfusate, more preferably between 1 µg/l Perfusate and 800 µg/l Perfusate.

Reference values for tPA have been defined, and either specific cut-off values for acceptable concentration of tPA could be used or the concentration could be followed over time during the isolated organ perfusion and the changes could be used to decide if the organ is well functioning or not. The analysis could be used on its own or in combination with other analysis. A combinatorial approach could improve sensitivity and/or specificity of the analysis as more organ functions are being tested.

For example the cut off reference values could be >4000 pg/ml and <7400 pg/ml or >3500 pg/ml and <7400 pg/ml or >4500 pg/ml and <7400 pg/ml or >4500 pg/ml and <8000 pg/ml or >4000 pg/ml and <8000 pg/ml or >3500 pg/ml and <8000 pg/ml. Alternatively a single cut off level could be used. These could be used to determine that the organ is selected for transplantation or for further treatment or analysis only if the concentration of tPA in the Perfusate is within these reference values.

TF/tPA ratio

The balance between pro-coagulation and fibrinolysis is important for the organ function. Therefore, a ratio between TF and tPA could also provide valuable information as a pro-coagulant/anti-coagulant ratio. Although we have shown this effect in lungs only, all organs contain vasculature and therefore release both substances to the Perfusate and the same relations is anticipated.

Other biomarkers relating to a thrombotic/antithrombotic or thrombotic/fibrinolytic state could be used to determine the function of an organ during isolated organ perfusion. Such biomarkers could involve analysis of D-dimer, von Willebrand Factor (vWF), Plasminogen activator inhibitor (PAI) etc. These biomarkers could be analyzed to determine organ function either on their own or in relation other biomarkers or in combination with other biomarkers.

Cell Rupture Markers—Background

Double stranded DNA (dsDNA) is normally contained in the cell nucleus. Its release to the circulation is an abnormal event. There are other intra-cellular components that are not released to the circulation in healthy tissue, such as mitochondrial DNA, ribosomes etc.

Cell Rupture Markers—In the Invention

Double stranded DNA (dsDNA) is a cell rupture marker and its presence in the Perfusate could be viewed as a sign of cell death within the organ. The cell death could either be due to necrosis or apoptosis and could be a response to hypoxia, which leads to swelling of the cells when the ion-pumps no longer have energy to work. The resulting burst of the cells causes release of intra-cellular products to the Perfusate. Measuring dsDNA in the Perfusate during isolated organ perfusion could generate information about organ function, where a high level of dsDNA represents more severe cell death within the organ. The organ could for example be a lung, a heart, a kidney a liver, a pancreases or a bowel. As an alternative, mitochondrial DNA or ribosomes could be used instead of dsDNA for the analysis.

dsDNA could be analyzed for using immunological methods or using a dsDNA specific nucleic acid stain, such as Picogreen®. In any case the assay used should deliver results within about an hour or more preferably within 30 minutes to be useful during the actual procedure.

Reference values can be defined and either a specific cut-off value for acceptable concentration of dsDNA could be used or the concentration could be followed over time during the isolated organ perfusion and the changes could be used to decide if the organ is well functioning or not. The analysis could be used on its own or in combination with other analysis. A combinatorial approach could improve sensitivity and/or specificity of the analysis as more organ functions are being tested.

For example, a reference value which is a cut off of 2000 ng/ml or 3000 ng/ml or 3500 ng/ml or 4000 ng/ml could be used. Preferably a cut off of 3000 ng/ml should be used. This would mean that if a concentration of cell rupture markers, especially dsDNA above the reference value cut off was detected, the organ would deselected for transplantation. Alternatively, the organ could be treated when the reference value is exceeded. Specifically, an anti-apoptotic agent could be added to the Perfusate. Examples of suitable anti-apoptotic agents include inhibitors of c-Myc, Bax, p53, tBid, BCL and caspase.

Surfactant Protein A and D—Background

Surfactant protein A and D (SpA and SpD) are water soluble proteins with immune activity and function as opsonins on the epithelial/alveolar side of the lung. SpA is an important immune modulator. Both SpA and SpD are large multimer proteins. Surfactant protein A is also involved in controlling the release of surfactants via exocytosis of lamellar bodies from Epithelial type II cells and to certain extend Clara cells in small airways. The effect on surfactant release of SpA is suppressive and its effect is opposed by SpD.

It has been shown that SpD is reduced in Bronchio-Alveolar Lavage (BAL) samples from COPD patients, but that it was increased in blood samples, indicating a leakage (see Stockley 2014). It has not before been tested in the Perfusate during isolated organ perfusion.

Surfactant Protein A and D—In the Invention

Leakage of surfactant protein A and D (SpA and SpD) from the alveolar side to the vasculature could be viewed as a sign of disruption of the air-liquid barrier in the lung. The more pronounced this disruption is the worse is the function of the lung. Measuring SpA and/or SpD in the Perfusate of an isolated lung would therefore generate information about the lung function.

SpA and SpD could be analyzed for using for example immunologic assays. In any case the assay used should deliver results within about an hour or more preferably within 30 minutes to be useful during the actual procedure.

Reference values can be defined, where either a specific cut-off value for acceptable concentration of SpA and/or SpD could be used or the concentration could be followed over time during the isolated lung perfusion and the changes could be used to decide if the organ is well functioning or not and therefore whether it should be selected for transplantation and/or treatment and/or further evaluation. The analysis could be used on its own or in combination with other analysis. A combinatorial approach could improve sensitivity and/or specificity of the analysis as more organ functions are being tested.

For example, the reference value could be a cut-off level of SpA in the Perfusate of above 10 µg/ml or above 30 µg/ml or above 40 µg/ml or above 60 µg/ml or above 80 µg/ml.

For example the reference value could be a cut off level of SpD in the Perfusate of above 50 ng/ml, or above 80 ng/ml or above 100 ng/ml or about 120 ng/ml or above 130 ng/ml or about 140 ng/ml or about 150 ng/ml or above 160 ng/ml or above 180 ng/ml or above 200 ng/ml.

Above the reference values the organ would be deselected for transplantation. At or below the reference value the organ could be selected for transplantation, treatment and/or further monitoring.

Combinatorial Analysis

Biomarkers including TF, tPA, dsDNA, SpA, SpD and any other potentially useful biomarkers could be used as individual biomarkers or they could be used in any combination to provide information about the organ function or well-being. A combination could comprise selection of at least two of the biomarkers TF, tPA, dsDNA, SpA and SpD or at least three of the biomarkers TF, tPA, dsDNA, SpA and SpD or at least four of the biomarkers TF, tPA, dsDNA, SpA and SpD. These analyses could also be combined with any other for the organ relevant biomarker or functionality test.

The SpA and SpD analysis are specific for lungs and are not relevant for other organs. TF, tPA and dsDNA are relevant either alone or in any combination for any organ during in vivo or ex vivo isolated organ perfusion.

The analysis could use reference values based on normal ranges, cut off values or concentration change over time. The analysis could also be used to monitor treatment of an organ. The treatment could comprise one or more anti-inflammatory substances and/or one or more anti-thrombotic substances and/or one or more anti-apoptotic substances.

EXAMPLES

TF in Perfusate 45 sets of human lungs were perfused ex vivo using STEEN Solution as the Perfusate. The perfusion was performed up to seven hours, although in most cases the perfusion was stopped after three or four hours, either to transplant the lung or to discard a lung that was not considered suitable for transplantation. The Perfusate was collected and frozen for subsequent immunologic analysis of TF. Samples were normally collected at the beginning and then every hour. However, not all cases had samples collected at every time point. This was attributed to the clinical situation where the sample collection was to take place. Taking care of the organ was the primary task collection of samples necessarily came second.

When the data is aggregated it can be shown that discarded lungs have a higher increase of TF then transplanted lungs. For each individual lung this is not always the case, and some transplanted lungs have values outside a suggested cut-off. Had the present invention been available, these lungs might have been deselected or preferably treated to become transplantable in relation to this parameter, if the analysis had been performed during EVLP. Such handling could have reduced IRI in the patient. Patient outcome data can be analysed to ensure that the reference values for organ selection, de-selection and treatment are optimised.

TABLE 1

| TF measurements in pg/ml of the Perfusate | | | | | | | | |
|---|---|---|---|---|---|---|---|---|
| 0 h | 1 h | 2 h | 3 h | 4 h | 5 h | 6 h | 7 h | organ |
|  | 31.91 |  | 88.97 |  |  |  |  | declined |
|  | 22.85 | 54.10 | 43.77 | 169.99 |  |  |  | declined |
|  | 87.94 | 79.86 | 90.52 |  |  |  |  | declined |
|  | 120.30 | 71.07 | 121.40 |  |  |  |  | declined |
|  | 9.66 | 38.73 | 66.17 | 67.23 |  |  |  | declined |
|  | 21.00 | 78.46 | 116.38 | 154.43 |  |  |  | declined |
|  | 223.35 | 322.26 | 365.68 | 385.59 |  |  |  | declined |
|  |  |  |  |  |  |  |  | declined |
| 7.13 | 67.07 | 92.41 | 173.66 | 223.71 |  |  |  | declined |
| 0.00 | 70.16 | 91.46 | 131.50 | 159.97 |  |  |  | declined |
| 0.00 | 42.49 | 60.80 | 75.19 | 92.34 |  |  |  | declined |
| 0.00 | 17.69 | 37.96 | 47.97 |  |  |  |  | declined |
| 16.29 | 63.22 | 81.19 | 106.32 | 166.61 | 204.21 | 323.95 |  | declined |
| 38.09 | 208.95 | 324.07 | 491.50 |  |  |  |  | declined |
| 4.20 | 146.06 | 233.02 | 304.50 | 332.58 | 328.70 |  |  | declined |
|  |  |  |  |  |  |  |  | accepted |
|  | 10.13 | 41.23 |  |  |  |  |  | accepted |
|  | 64.42 | 103.97 |  |  |  |  |  | accepted |
|  | 0.00 | 13.25 |  |  |  |  |  | accepted |
|  | 262.33 | 288.53 |  |  |  |  |  | accepted |
|  | 293.31 | 7.19 | 57.10 |  |  |  |  | accepted |
|  | 164.29 | 172.92 | 170.82 |  |  |  |  | accepted |
|  | 16.00 | 94.81 | 146.55 |  |  |  |  | accepted |
|  | 159.37 | 0.00 | 14.95 |  |  |  |  | accepted |
|  | 13.37 | 31.29 | 50.21 | 86.73 |  |  |  | accepted |
|  | 7.30 | 20.07 | 29.65 |  |  |  |  | accepted |
|  | 81.14 | 196.16 | 256.40 | 306.02 |  |  |  | accepted |
|  | 20.21 | 55.14 | 72.65 | 97.13 | 103.08 | 123.14 |  | accepted |
|  | 18.25 | 38.46 | 78.77 | 96.59 | 113.31 |  |  | accepted |
|  |  |  |  |  |  |  |  | accepted |
|  | 24.86 | 70.97 | 98.48 | 128.72 | 196.80 |  |  | accepted |
|  | 72.23 | 115.40 | 184.69 |  |  |  |  | accepted |
|  | 110.12 | 142.76 | 192.93 | 208.06 | 179.10 | 249.40 | 181.64 | accepted |
| 36.61 | 33.77 | 38.85 | 50.44 | 63.58 | 60.32 |  |  | accepted |
| 36.35 | 24.88 | 44.93 | 71.58 | 105.26 |  |  |  | accepted |

TABLE 1-continued

| \multicolumn{9}{c}{TF measurements in pg/ml of the Perfusate} |
|---|---|---|---|---|---|---|---|---|

| 0 h | 1 h | 2 h | 3 h | 4 h | 5 h | 6 h | 7 h | organ |
|---|---|---|---|---|---|---|---|---|
| 4.75 | 82.02 | 149.87 | 198.98 | 259.29 | | | | accepted |
| 0.00 | 27.69 | 32.16 | 53.09 | 66.12 | | | | accepted |
| 0.00 | 11.69 | 43.18 | 58.00 | 66.38 | 77.60 | | | accepted |
| 0.00 | 42.70 | 64.21 | 76.32 | 120.30 | | 114.17 | 144.63 | accepted |
| 7.88 | 165.07 | 97.78 | 296.54 | 267.52 | 386.54 | 424.37 | | accepted |
| 0.00 | 19.49 | 15.76 | 13.87 | 23.91 | | | | accepted |
| | | | | | | | | accepted |
| 0.00 | 146.61 | 207.46 | 231.52 | | | | | accepted |
| | | | | | | | | accepted |
| 0.00 | 23.08 | 27.22 | 31.17 | | | | | accepted |

As values generally are increasing over time the increase rate or change could be an alternative measure of organ function or well-being. This ongoing increase could also be viewed as an opportunity to treat and to monitor the effect of the treatment.

t-PA in Perfusate 45 sets of human lungs were perfused ex vivo using STEEN Solution as the Perfusate. The perfusion was performed up to seven hours, although in most cases the perfusion was stopped after three or four hours, either to transplant the lung or to discard a lung that was not considered suitable for transplantation. The Perfusate was collected and frozen for subsequent immunologic analysis of tPA. Samples were normally collected at the beginning and then every hour. However, not all cases had samples collected at every time point. This was attributed to the clinical situation where the sample collection was to take place. Taking care of the organ was the primary task collection of samples necessarily came second.

When the data is aggregated it can be shown that discarded lungs have a higher increase of tPA then transplanted lungs. For each individual lung this is not always the case, and some transplanted lungs have values outside a suggested cut-off. Had the present invention been available, these lungs might have been deselected or preferably treated to become transplantable in relation to this parameter, if the analysis had been performed during EVLP. Such handling could have reduced IRI in the patient. Patient outcome data can be analysed to ensure that the reference values for organ selection, de-selection and treatment are optimised.

TABLE 2

| \multicolumn{9}{c}{tPA measurements in pg/ml of the Perfusate} |
|---|---|---|---|---|---|---|---|---|

| 0 h | 1 h | 2 h | 3 h | 4 h | 5 h | 6 h | 7 h | organ |
|---|---|---|---|---|---|---|---|---|
| | | 3777.56 | | 5384.14 | | | | declined |
| | 879.58 | 943.03 | 941.73 | 855.51 | | | | declined |
| | 1683.63 | 2136.95 | 4438.94 | | | | | declined |
| | 1703.68 | 5790.37 | 4712.17 | | | | | declined |
| | 1336.10 | 1977.21 | 2102.23 | 2083.04 | | | | declined |
| | 1918.55 | 3893.91 | 4853.80 | 6689.55 | | | | declined |
| | 7432.13 | 7938.39 | 7253.58 | 5355.06 | | | | declined |
| | | | | | | | | declined |
| 430.34 | 3257.01 | 2584.35 | 2897.33 | 2796.27 | | | | declined |
| 0.00 | 4016.74 | 4593.77 | 3986.61 | 4361.89 | | | | declined |
| 398.03 | 6399.09 | 7990.92 | 6488.13 | 7543.51 | | | | declined |
| 0.00 | 5208.32 | 5682.91 | 5501.72 | | | | | declined |
| 241.29 | 3194.87 | 2877.31 | 2426.62 | 2337.44 | 2570.51 | 2247.35 | | declined |
| 767.16 | 6001.87 | 5986.54 | 6138.44 | | | | | declined |
| 935.74 | 3736.28 | 5503.47 | 5864.36 | 6740.49 | 7985.56 | | | declined |
| | | | | | | | | accepted |
| | 3136.26 | 3248.58 | | | | | | accepted |
| | 4023.00 | 5125.07 | | | | | | accepted |
| | 5056.81 | 6021.62 | | | | | | accepted |
| | 1117.76 | 1587.08 | | | | | | accepted |
| | 3347.04 | 4186.86 | 2876.53 | | | | | accepted |
| | 1915.08 | 2614.31 | 1533.15 | | | | | accepted |
| | 1663.00 | 937.54 | 939.05 | | | | | accepted |
| | 839.74 | 1783.82 | 2465.14 | | | | | accepted |
| | 4088.67 | 5322.91 | 4862.44 | 4660.87 | | | | accepted |
| | 3836.53 | 6585.05 | 7373.57 | | | | | accepted |
| | 3212.77 | 4404.40 | 4342.36 | 4876.13 | | | | accepted |
| | 5435.67 | 1546.03 | 2763.98 | 3783.41 | 3964.12 | 5312.81 | | accepted |
| | 6944.47 | 12700.75 | 15379.76 | 15865.16 | 15151.89 | | | accepted |
| | | | | | | | | accepted |
| | 2977.88 | 5040.24 | 5125.40 | 5357.70 | 7035.02 | | | accepted |
| | 4592.32 | 11231.66 | 15692.95 | | | | | accepted |
| | 4137.27 | 6236.47 | 6891.88 | 5765.68 | 5447.62 | 7494.27 | 5643.63 | accepted |
| 1833.14 | 4941.38 | 4423.87 | 4526.78 | 3613.11 | 3162.26 | | | accepted |
| 3141.42 | 7667.48 | 6657.33 | 5205.01 | 4502.16 | | | | accepted |
| 2530.74 | 10490.55 | 11881.73 | 10021.23 | 7910.35 | | | | accepted |
| 176.75 | 2326.03 | 2756.56 | 3239.84 | 3025.57 | | | | accepted |

TABLE 2-continued

| tPA measurements in pg/ml of the Perfusate | | | | | | | | |
|---|---|---|---|---|---|---|---|---|
| 0 h | 1 h | 2 h | 3 h | 4 h | 5 h | 6 h | 7 h | organ |
| 0.00 | 5028.39 | 6186.85 | 5616.74 | 5772.45 | 11987.98 | | | accepted |
| 840.26 | 4640.46 | 5596.86 | 7104.82 | 7171.21 | 5773.25 | 5216.30 | 6222.62 | accepted |
| 313.12 | 4029.61 | 3873.02 | 5092.38 | 4108.83 | 5374.34 | 5642.49 | | accepted |
| 528.44 | 2534.90 | 2492.89 | 4734.83 | 7065.58 | | | | accepted |
| | | | | | | | | accepted |
| 0.00 | 4613.07 | 5516.09 | 5153.39 | | | | | accepted |
| | | | | | | | | accepted |
| 961.90 | 3214.58 | 3547.92 | 3841.02 | | | | | accepted |

As values generally are increasing over time the increase rate or change could be an alternative measure of organ function or well-being. This ongoing increase could also be viewed as an opportunity to treat and to monitor the effect of the treatment.

dsDNA in Perfusate 45 sets of human lungs were perfused ex vivo using STEEN Solution as the Perfusate. The perfusion was performed up to seven hours, although in most cases the perfusion was stopped after three or four hours, either to transplant the lung or to discard a lung that was not considered suitable for transplantation. The Perfusate was collected and frozen for subsequent Picogreen® analysis of dsDNA. Samples were normally collected at the beginning and then every hour. However, not all cases had samples collected at every time point. This was attributed to the clinical situation where the sample collection was to take place. Taking care of the organ was the primary task collection of samples necessarily came second.

When the data is aggregated it can be shown that discarded lungs have a higher increase of dsDNA then transplanted lungs. For each individual lung this is not always the case, and some transplanted lungs have values outside a suggested cut-off. Had the present invention been available, these lungs might have been deselected or preferably treated to become transplantable in relation to this parameter, if the analysis had been performed during EVLP. Such handling could have reduced IRI in the patient. Patient outcome data can be analysed to ensure that the reference values for organ selection, de-selection and treatment are optimised.

TABLE 3

| dsDNA measurements in ng/ml of Perfusate | | | | | | | | |
|---|---|---|---|---|---|---|---|---|
| 0 h | 1 h | 2 h | 3 h | 4 h | 5 h | 6 h | 7 h | Organ |
| | 3351.61 | | 2652.00 | | | | | declined |
| | 1929.11 | 4014.69 | 2432.01 | 2764.90 | | | | declined |
| | 2068.92 | 2828.14 | 3706.76 | | | | | declined |
| | 2294.55 | 2091.25 | 2550.91 | | | | | declined |
| | 2072.14 | 1880.26 | 2148.40 | 2101.32 | | | | declined |
| | 2919.62 | 2468.00 | 2899.03 | 3866.57 | | | | declined |
| | 4399.79 | 3512.96 | 2590.85 | 3042.50 | | | | declined |
| | | | | | | | | declined |
| 1354.52 | 2961.90 | 2400.07 | 2864.60 | 2763.92 | | | | declined |
| 0.00 | 2792.65 | 3625.94 | 3362.22 | 3838.20 | | | | declined |
| 6083.89 | 5141.59 | 5282.45 | 5206.10 | 5957.51 | | | | declined |
| 876.41 | 4844.63 | 2713.91 | 2793.33 | | | | | declined |
| 1698.83 | 3459.91 | 2816.06 | 3254.08 | 3398.37 | 3934.10 | 7095.66 | | declined |
| 3195.03 | 3491.15 | 4082.85 | 5471.88 | | | | | declined |
| 772.53 | 5072.57 | 3905.25 | 3437.58 | 3716.36 | 4205.11 | | | declined |
| | | | | | | | | accepted |
| | 2361.27 | | | | | | | accepted |
| | 2974.63 | 5102.48 | | | | | | accepted |
| | 1796.46 | 1772.94 | | | | | | accepted |
| | 2061.10 | 2091.32 | | | | | | accepted |
| | 2012.44 | 1728.12 | 2195.58 | | | | | accepted |
| | 4034.23 | 3557.27 | 3355.15 | | | | | accepted |
| | 1884.06 | 1768.12 | 1652.62 | | | | | accepted |
| | 3188.16 | 2749.55 | 2412.26 | | | | | accepted |
| | 1628.30 | 1715.33 | 1954.07 | 1892.17 | | | | accepted |
| | 2506.70 | 2201.62 | 2128.31 | | | | | accepted |
| | 2224.69 | 2408.96 | 2830.47 | 2776.52 | | | | accepted |
| | 2689.91 | 2424.20 | 2534.47 | 2684.60 | 2826.81 | 3002.24 | | accepted |
| | 2252.21 | 2763.03 | 3007.67 | 3656.27 | 4050.26 | | | accepted |
| | | | | | | | | accepted |
| | 3237.17 | 2172.47 | 2426.69 | 1968.41 | 1986.35 | | | accepted |
| | 1907.78 | 1782.67 | 2048.01 | | | | | accepted |
| | 3818.21 | 2825.60 | 3363.31 | 3575.60 | 2985.23 | 2485.11 | 2770.65 | accepted |
| 1767.19 | 2118.28 | 1885.33 | 2246.49 | 2413.49 | 2667.52 | | | accepted |
| 1912.86 | 1503.38 | 1273.46 | 1527.16 | 1617.38 | | | | accepted |
| 1896.25 | 2978.20 | 2427.69 | 2661.35 | 2458.53 | | | | accepted |
| 1232.15 | 2717.87 | 2189.24 | 1971.25 | 2113.11 | | | | accepted |
| 782.99 | 1565.07 | 1832.19 | 1994.63 | 2057.26 | 2031.05 | | | accepted |
| 1777.66 | 3101.46 | 3260.42 | 3547.90 | 3616.16 | 3830.36 | 3294.70 | 3070.39 | accepted |

TABLE 3-continued

| \multicolumn{9}{c}{dsDNA measurements in ng/ml of Perfusate} |
|---|---|---|---|---|---|---|---|---|
| 0 h | 1 h | 2 h | 3 h | 4 h | 5 h | 6 h | 7 h | Organ |
| 1128.96 | 1579.45 | 1598.58 | 2180.42 | 2308.22 | 2561.03 | 2569.89 | | accepted |
| 1473.41 | 3876.25 | 2862.39 | 2369.72 | 2515.82 | | | | accepted |
| | | | | | | | | accepted |
| | 873.16 | 3268.29 | 2788.61 | 2917.00 | | | | accepted |
| | | | | | | | | accepted |
| 1887.96 | 3017.24 | 2404.47 | 2833.45 | | | | | accepted |

As values generally are increasing over time the increase rate or change could be an alternative measure of organ function or well-being. This ongoing increase could also be viewed as an opportunity to treat and to monitor the effect of the treatment.

SpA in the Perfusate 45 sets of human lungs were perfused ex vivo using STEEN Solution as the Perfusate. The perfusion was performed up to seven hours, although in most cases the perfusion was stopped after three or four hours, either to transplant the lung or to discard a lung that was not considered suitable for transplantation. The Perfusate was collected and frozen for subsequent immunologic analysis of SpA. Samples were normally collected at the beginning and then every hour. However, not all cases had samples collected at every time point. This was attributed to the clinical situation where the sample collection was to take place. Taking care of the organ was the primary task collection of samples necessarily came second.

In this data set there is no difference in the aggregated data comparing transplanted and non-transplanted lungs. This shows that the evaluation that was used (physical examination only) was not sophisticated enough to take into account the level of disruption of the air-liquid barrier in the lung which can be indicated by SpA concentrations. Had the present invention been available, these lungs might have been deselected or preferably treated to become transplantable in relation to this parameter, if the analysis had been performed during EVLP. Such handling could have reduced IRI in the patient. Patient outcome data can be analysed to ensure that the reference values for organ selection, deselection and treatment are optimised.

TABLE 4

| \multicolumn{9}{c}{SpA measurements in ng/ml of Perfusate} |
|---|---|---|---|---|---|---|---|---|
| 0 h | 1 h | 2 h | 3 h | 4 h | 5 h | 6 h | 7 h | Organ |
| | 9152.13 | | 16148.89 | | | | | declined |
| | 20157.33 | 23838.28 | 30857.76 | 31186.67 | | | | declined |
| | 14305.32 | 21963.70 | 31843.25 | | | | | declined |
| | 9052.32 | 13069.81 | 19557.32 | | | | | declined |
| | 9530.64 | 13620.03 | 14051.07 | 21896.35 | | | | declined |
| | 9361.99 | 11266.53 | 16025.32 | 22841.02 | | | | declined |
| | 53923.39 | 60871.32 | 93942.84 | 86619.55 | | | | declined |
| | | | | | | | | declined |
| 8990.92 | 20377.47 | 17945.88 | 27567.28 | 32562.48 | | | | declined |
| 5559.87 | 26051.10 | 23286.72 | 25423.03 | 28513.43 | | | | declined |
| 13559.01 | 64573.39 | 82503.76 | 94217.64 | 98648.69 | | | | declined |
| 7155.80 | 12096.47 | 11241.62 | 14511.25 | | | | | declined |
| 12279.58 | 29623.49 | 31951.04 | 36158.27 | 38509.89 | 44552.09 | 46237.21 | | declined |
| 9134.08 | 51035.16 | 51031.72 | 59158.28 | | | | | declined |
| | 16984.87 | 19371.24 | 19344.75 | 20256.73 | 22861.66 | | | declined |
| | | | | | | | | accepted |
| | 16179.11 | 16900.94 | | | | | | accepted |
| | 9405.44 | 32796.27 | | | | | | accepted |
| | 15443.48 | 18948.95 | | | | | | accepted |
| | 20304.81 | 23888.11 | | | | | | accepted |
| | 28519.24 | 29130.75 | 36521.00 | | | | | accepted |
| | 34447.00 | 52603.33 | 51643.86 | | | | | accepted |
| | 9027.59 | 11935.70 | 11962.78 | | | | | accepted |
| | 23675.90 | 27402.81 | 35086.67 | | | | | accepted |
| | 5525.06 | 8185.53 | 8060.64 | 11447.68 | | | | accepted |
| | 19477.78 | 25817.31 | 30299.42 | | | | | accepted |
| | 8405.31 | 13416.43 | 16058.85 | 14295.34 | | | | accepted |
| | 18250.19 | 31222.98 | 39436.48 | 50927.36 | 61885.30 | 59559.90 | | accepted |
| | 10030.40 | 18999.08 | 27426.42 | 46642.65 | 46925.17 | | | accepted |
| | | | | | | | | accepted |
| | 10974.69 | 24050.20 | 26337.18 | 26080.33 | 40907.46 | | | accepted |
| | 34069.01 | 42497.74 | 52032.80 | | | | | accepted |
| | 78994.07 | 89109.23 | | 99087.85 | | | | accepted |
| 20164.97 | 25035.55 | 24845.60 | 36354.87 | 48412.45 | 46979.62 | | | accepted |
| 23258.29 | 19109.92 | 25065.47 | 24798.68 | 39213.84 | | | | accepted |
| 10865.43 | 17016.85 | 25328.17 | 33960.98 | 48981.27 | | | | accepted |
| 7114.22 | 14889.33 | 15927.86 | 26929.96 | 25121.19 | | | | accepted |
| 5374.27 | 5813.65 | 7946.32 | 7149.33 | 6885.78 | 6933.40 | | | accepted |
| 9933.56 | 38754.72 | 66658.29 | 65827.77 | 70795.37 | 74030.61 | 64239.23 | 91058.89 | accepted |
| 11724.36 | 34389.58 | 32568.83 | 46673.38 | 42223.06 | 51856.43 | 47165.93 | | accepted |

TABLE 4-continued

| SpA measurements in ng/ml of Perfusate | | | | | | | | |
|---|---|---|---|---|---|---|---|---|
| 0 h | 1 h | 2 h | 3 h | 4 h | 5 h | 6 h | 7 h | Organ |
| 6176.87 | 11085.40 | 12203.34 | 12874.15 | 17626.89 | | | | accepted |
| | | | | | | | | accepted |
| 1747.71 | 49133.64 | 63259.26 | 74911.60 | | | | | accepted |
| | | | | | | | | accepted |
| 6676.88 | 14594.30 | 17667.02 | 20964.21 | | | | | accepted |

As values generally are increasing over time the increase rate or change could be an alternative measure of organ function or well-being. This ongoing increase could also be viewed as an opportunity to treat and to monitor the effect of the treatment.

SpD in the Perfusate 45 sets of human lungs were perfused ex vivo using STEEN Solution as the Perfusate. The perfusion was performed up to seven hours, although in most cases the perfusion was stopped after three or four hours, either to transplant the lung or to discard a lung that was not considered suitable for transplantation. The Perfusate was collected and frozen for subsequent immunologic analysis of SpD. Samples were normally collected at the beginning and then every hour. However, not all cases had samples collected at every time point. This was attributed to the clinical situation where the sample collection was to take place. Taking care of the organ was the primary task collection of samples necessarily came second.

When the data is aggregated it can be shown that discarded lungs have a higher increase of SpD then transplanted lungs. For each individual lung this is not always the case, and some transplanted lungs have values outside a suggested cut-off. Had the present invention been available, these lungs might have been deselected or preferably treated to become transplantable in relation to this parameter, if the analysis had been performed during EVLP. Such handling could have reduced IRI in the patient. Patient outcome data can be analysed to ensure that the reference values for organ selection, de-selection and treatment are optimised.

TABLE 5

| SpD measurements in ng/ml of Perfusate | | | | | | | | |
|---|---|---|---|---|---|---|---|---|
| 0 h | 1 h | 2 h | 3 h | 4 h | 5 h | 6 h | 7 h | Organ |
| | | 0.00 | 154.43 | | | | | declined |
| | 72.68 | 134.73 | 130.37 | 132.73 | | | | declined |
| | 0.00 | 0.00 | 85.78 | | | | | declined |
| | 0.00 | 24.41 | 76.51 | | | | | declined |
| | 10.13 | 41.23 | 64.42 | 103.97 | | | | declined |
| | 16.00 | 94.81 | 146.55 | 159.37 | | | | declined |
| | 256.24 | 278.62 | 308.92 | 316.29 | | | | declined |
| | | | | | | | | declined |
| 0.00 | 58.88 | 102.63 | 189.59 | 187.82 | | | | declined |
| 0.00 | 135.00 | 185.30 | 187.91 | 213.95 | | | | declined |
| 12.17 | 92.75 | 151.75 | 154.87 | 179.32 | | | | declined |
| 0.00 | 11.13 | 25.09 | 25.23 | | | | | declined |
| 6.96 | 13.63 | 9.15 | 55.75 | 107.56 | 80.67 | 145.72 | | declined |
| 21.01 | 39.49 | 91.83 | 156.04 | | | | | declined |
| | 52.15 | 132.14 | 120.02 | 180.98 | 152.45 | | | declined |
| | | | | | | | | accepted |
| | | | | | | | | accepted |
| | | | | | | | | accepted |
| | 22.13 | 103.01 | | | | | | accepted |
| | 44.29 | 29.11 | | | | | | accepted |
| | 22.74 | 0.00 | 35.47 | | | | | accepted |
| | 94.07 | 79.59 | 56.01 | | | | | accepted |
| | 0.00 | 35.38 | 32.23 | | | | | accepted |
| | 8.88 | 28.19 | 60.64 | | | | | accepted |
| | 0.00 | 13.25 | 31.91 | 88.97 | | | | accepted |
| | 22.85 | 54.10 | 43.77 | | | | | accepted |
| | 169.99 | 262.33 | 288.53 | 293.31 | | | | accepted |
| | 7.19 | 57.10 | 87.94 | 79.86 | 90.52 | 120.30 | | accepted |
| | 71.07 | 121.40 | 164.29 | 172.92 | 170.82 | | | accepted |
| | | | | | | | | accepted |
| | 0.00 | 14.95 | 40.24 | 50.04 | 63.65 | | | accepted |
| | 62.80 | 65.95 | 130.66 | | | | | accepted |
| | 54.38 | 102.18 | 132.60 | 149.00 | 154.49 | 201.17 | 164.16 | accepted |
| 49.65 | 12.69 | 29.07 | 30.15 | 45.22 | 55.47 | | | accepted |
| 0.00 | 0.00 | 0.00 | 11.25 | 52.12 | | | | accepted |
| 0.00 | 108.60 | 167.75 | 210.42 | 224.94 | | | | accepted |
| 0.00 | 71.83 | 168.38 | 182.22 | 189.97 | | | | accepted |
| 0.00 | 0.00 | 33.37 | 44.28 | 56.54 | 86.76 | | | accepted |
| 0.00 | 0.00 | 25.04 | 24.13 | 53.46 | 51.32 | 76.27 | 76.27 | accepted |
| 0.00 | 73.09 | 123.46 | 203.03 | 236.11 | 245.20 | 263.22 | | accepted |
| 0.00 | 0.00 | 0.00 | 0.00 | 16.53 | | | | accepted |
| | | | | | | | | accepted |

TABLE 5-continued

| SpD measurements in ng/ml of Perfusate | | | | | | | | |
|---|---|---|---|---|---|---|---|---|
| 0 h | 1 h | 2 h | 3 h | 4 h | 5 h | 6 h | 7 h | Organ |
| 0.00 | 15.66 | 80.51 | 99.24 | | | | | accepted |
| 0.00 | 0.00 | 11.39 | 18.80 | | | | | accepted accepted |

As values generally are increasing over time the increase rate or change could be an alternative measure of organ function or well-being. This ongoing increase could also be viewed as an opportunity to treat and to monitor the effect of the treatment.

Aggregated Analysis

The different analysis were analyzed together using the following suggested cut off values:
TF >120 pg/ml
tPA >4000 and <7400 pg/ml
dsDNA >3000 ng/ml
SpA >40 000 ng/ml
SpD >130 ng/ml

TABLE 6

Aggregated analysis, in which the value is the order of the perfused lung

| TF | tPA | dsDNA | SpA | SpD | organ |
|---|---|---|---|---|---|
| 5* | 5* | 5** | 5* | 5** | declined |
| 6** | 6** | 6** | 6* | 6** | declined |
| 9* | 9* | 9** | 9* | 9* | declined |
| 10** | 10* | 10* | 10* | 10* | declined |
| 14* | 14** | 14* | 14* | 14* | declined |
| 21** | 21* | 21** | 21* | 21** | declined |
| 24** | 24** | 24** | 24** | 24** | declined |
| 29** | 29** | 29* | 29* | 29** | declined |
| 33** | 33* | 33** | 33* | 33** | declined |
| 36* | 36** | 36** | 36** | 36** | declined |
| 38* | 38* | 38** | 38* | 38* | declined |
| 39** | 39** | 39** | 39** | 39** | declined |
| 40** | 40* | 40** | 40* | 40** | declined |
| 41** | 41** | 41** | 41** | 41** | declined |
| 2 | 2** | 2 | 2 | 2 | accepted |
| 3 | 3 | 3** | 3 | 3 | accepted |
| 4 | 4 | 4 | 4 | 4 | accepted |
| 7** | 7** | 7 | 7 | 7 | accepted |
| 8** | 8 | 8 | 8 | 8 | accepted |
| 11** | 11** | 11** | 11** | 11 | accepted |
| 12 | 12** | 12 | 12 | 12 | accepted |
| 13** | 13** | 13** | 13 | 13 | accepted |
| 15 | 15 | 15 | 15 | 15 | accepted |
| 16 | 16 | 16 | 16 | 16 | accepted |
| 17** | 17 | 17 | 17 | 17** | accepted |
| 18 | 18 | 18** | 18** | 18 | accepted |
| 19 | 19** | 19** | 19** | 19** | accepted |
| 22** | 22 | 22** | 22** | 22 | accepted |
| 23** | 23** | 23 | 23** | 23** | accepted |
| 25** | 25** | 25** | 25** | 25** | accepted |
| 26 | 26 | 26 | 26** | 26 | accepted |
| 28 | 28 | 28 | 28 | 28 | accepted |
| 30** | 30** | 30 | 30** | 30** | accepted |
| 31 | 31** | 31 | 31 | 31** | accepted |
| 32 | 32** | 32 | 32 | 32 | accepted |
| 34 | 34 | 34** | 34** | 34 | accepted |
| 35** | 35 | 35 | 35** | 35** | accepted |
| 37 | 37 | 37 | 37 | 37 | accepted |
| 43** | 43 | 43 | 43** | 43 | accepted |
| 45 | 45** | 45** | 45 | 45 | accepted |

*Max 1 value outside of cut off reference value.
**At least 3 values outside of cut off reference value.

With these cut off reference values, there is a difference between the percentage of lungs with 0, at least 1 or at least 3 values outside the cut off. It can also be seen that in many occasions, these biomarkers co-exists, indicating that they are biomarkers of organ distress or dysfunction.

TABLE 7 summary of results for aggregated analysis

| outside cut off | declined | accepted |
|---|---|---|
| 0 values | 0% | 19% |
| max 1 value | 14% | 31% |
| at least 3 values | 64% | 50% |

As the cut off reference values are further optimized the number of false positive and false negatives will change. However, the examples demonstrate that indications that will be available using the present invention from biomarkers selected for evaluation are correlated to decisions currently being made based on the appearance of the organs. The aggregated data clearly show that evaluation according to the invention is correlated with lungs that were declined and lungs that were accepted for transplantation. It is anticipated that with the help of the present invention, clinicians would be able to make even better decisions about the prospects of any particular organ for transplantation.

A further correlation with clinical data would be used to optimize the cut-off levels. It is anticipated that the patients receiving the lungs with more values outside the ranges or cut offs did not do as well as patients receiving lungs with all values within the ranges or cut offs.

What is claimed is:

1. A method of treating an isolated organ with existing damage during isolated organ perfusion, wherein the isolated organ is determined during the method to be an isolated organ with existing damage based on comprising cells that have ruptured, the method comprising steps of:
perfusing the isolated organ with a perfusate;
measuring a concentration of a cell rupture marker in the perfusate during the perfusing of the isolated organ;
comparing the concentration of the cell rupture marker in the perfusate to a reference value of the cell rupture marker, as the perfusing of the isolated organ continues, to identify the isolated organ as comprising cells that have ruptured;
adding a tissue factor (TF) suppressor molecule to the perfusate, as the perfusing of the isolated organ continues, only after having identified the isolated organ as comprising cells that have ruptured; and
further perfusing the isolated organ with the perfusate after the TF suppressor molecule has been added, thereby treating the isolated organ, wherein
the cell rupture marker comprises one or more of double stranded DNA (dsDNA), mitochondrial DNA, or ribosomes; and
the TF suppressor molecule comprises a cyclooxygenase (COX) inhibitor.

2. The method according to claim 1, wherein the COX inhibitor comprises one or more of aspirin, naproxen, ibuprofen, or their equivalents.

3. The method according to claim 2, wherein the COX inhibitor comprises aspirin.

4. The method according to claim 1, wherein the step of adding the TF suppressor molecule to the perfusate as the perfusing of the isolated organ continues comprises adding the COX inhibitor to the perfusate to a concentration of 1 mg/L to 10 g/L.

5. The method according to claim 1, wherein the isolated organ is from an animal or a human being and is a lung or lungs, a kidney, a liver, a heart, a pancreas or a bowel.

6. The method according to claim 1, wherein the isolated organ is circulatorily isolated in vivo or is circulatorily isolated ex vivo.

7. The method according to claim 1, further comprising, after the step of comparing the concentration of the cell rupture marker in the perfusate to the reference value of the cell rupture marker to identify the isolated organ as comprising cells that have ruptured, a step of adding an anti-apoptotic agent to the perfusate.

8. The method according to claim 7, wherein the anti-apoptotic agent comprises one or more inhibitors of c-Myc, Bax, p53, tBid, BCL, or caspase.

9. The method according to claim 1, further comprising, after the step of comparing the concentration of the cell rupture marker in the perfusate to the reference value of the cell rupture marker to identify the isolated organ as comprising cells that have ruptured, a step of adding a fibrinolytic agent to the perfusate.

10. The method according to claim 9, wherein the fibrinolytic agent comprises one or more of Streptokinase or tPA.

11. The method according to claim 1, wherein the reference value of the cell rupture marker is at least 2,000 ng of the cell rupture marker per ml of the perfusate.

12. The method according to claim 1, wherein the cell rupture marker comprises dsDNA, the concentration of the cell rupture marker in the perfusate comprises a concentration of the dsDNA in the perfusate, and the reference value of the cell rupture marker comprises a reference value of dsDNA.

13. The method according to claim 12, wherein the reference value of dsDNA is at least 2,000 ng of dsDNA per ml of the perfusate.

14. The method according to claim 1, wherein the step of measuring the concentration of the cell rupture marker in the perfusate is conducted continuously over a predetermined time period or repeatedly at predetermined intervals.

15. The method according to claim 1, further comprising, after the step of perfusing the isolated organ with a perfusate, a step of measuring a concentration of one or more of TF, tPA, SpA, or SpD in the perfusate.

16. The method according to claim 1, wherein the isolated organ had been under stress in a donor of the isolated organ.

17. The method according to claim 1, wherein the isolated organ is from a donor who had experienced systemic effects of brain death or circulatory arrest.

* * * * *

UNITED STATES PATENT AND TRADEMARK OFFICE
CERTIFICATE OF CORRECTION

PATENT NO. : 12,216,114 B2
APPLICATION NO. : 17/150202
DATED : February 4, 2025
INVENTOR(S) : Magnus Nilsson and Anne-Li Sigvardsson It is certified that error appears in the above-identified patent and that said Letters Patent is hereby corrected as shown below:

In the Claims

Column 23; Lines 2-3, Claim 2, "aspirin, naproxen, ibuprofen, or their equivalents" should read --aspirin, naproxen or ibuprofen--

Signed and Sealed this
First Day of April, 2025

Coke Morgan Stewart
*Acting Director of the United States Patent and Trademark Office*